(12) United States Patent
Higuchi

(10) Patent No.: US 10,922,523 B2
(45) Date of Patent: *Feb. 16, 2021

(54) AUTHENTICATION USING PRISM

(71) Applicant: NEC Corporation, Tokyo (JP)

(72) Inventor: Teruyuki Higuchi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 49 days.

This patent is subject to a terminal disclaimer.

(21) Appl. No.: 16/124,815

(22) Filed: Sep. 7, 2018

(65) Prior Publication Data

US 2019/0005298 A1 Jan. 3, 2019

Related U.S. Application Data

(63) Continuation of application No. 15/854,217, filed on Dec. 26, 2017, which is a continuation of application
(Continued)

(30) Foreign Application Priority Data

Mar. 25, 2011 (JP) .................................. 2011-068705

(51) Int. Cl.
*G06K 9/00* (2006.01)
*A61B 5/1172* (2016.01)

(52) U.S. Cl.
CPC ........ *G06K 9/00046* (2013.01); *A61B 5/1172* (2013.01)

(58) Field of Classification Search
CPC ..... G06F 3/0488; G06F 21/32; A61B 5/1172; H04B 10/116; G05D 1/0242; G06K 9/00046
See application file for complete search history.

(56) References Cited

U.S. PATENT DOCUMENTS 4,811,414 A * 3/1989 Fishbine .............. A61B 5/1172
348/615
5,233,404 A * 8/1993 Lougheed .......... G06K 9/00046
250/227.19
(Continued)

FOREIGN PATENT DOCUMENTS

CN 1495659 A 5/2004
CN 101004789 A 7/2007
(Continued)

OTHER PUBLICATIONS

International Search Report for PCT Application No. PCT/JP2012/057346 dated Apr. 24, 2012.
(Continued)

*Primary Examiner* — Shaghayegh Azima

(57) ABSTRACT

A prism includes a large surface at least a portion of which is a placing region for a finger, a small surface parallel to the large surface, and first and second inclined lateral surfaces. A light source emits light to the first inclined lateral surface. A first imaging sensor arranged below the small surface receives a light transmitted from the light source through the small surface to obtain a first image. A second imaging sensor receives a light transmitted from the light source through the second inclined lateral surface to obtain a second image of which fingerprint pattern contrast is enhanced more than that of the first image. An infrared light source emits infrared ray light to the finger. The first imaging sensor receives the infrared ray light transmitted from the infrared light source through the small surface to obtain a third image for a blood vessel of the finger.

12 Claims, 5 Drawing Sheets

Related U.S. Application Data

No. 14/007,177, filed as application No. PCT/JP2012/057346 on Mar. 22, 2012, now Pat. No. 9,886,618.

(56) References Cited

U.S. PATENT DOCUMENTS

| | | | | |
|---|---|---|---|---|
| 5,426,296 A * | 6/1995 | Shikai | ................ | G06K 9/00046 250/227.2 |
| 5,509,083 A | 4/1996 | Abtahi et al. | | |
| 5,650,842 A * | 7/1997 | Maase | ................ | G06K 9/00046 356/71 |
| 5,822,445 A * | 10/1998 | Wong | ................ | G06K 9/00046 382/127 |
| 6,381,347 B1 | 4/2002 | Teng et al. | | |
| 6,643,390 B1 * | 11/2003 | Clark | ................ | G06K 9/00046 356/71 |
| 6,665,427 B1 * | 12/2003 | Keagy | ................ | G06K 9/00046 382/124 |
| 6,891,962 B1 * | 5/2005 | Kuno | ................ | G06K 9/00046 356/71 |
| 7,327,859 B1 * | 2/2008 | Chau | ................ | G06K 9/00046 382/116 |
| 8,229,185 B2 | 7/2012 | Ennis et al. | | |
| 8,768,015 B2 | 7/2014 | Higuchi | | |
| 2003/0025897 A1 * | 2/2003 | Iwai | ................ | G06K 9/00899 356/71 |
| 2003/0103686 A1 * | 6/2003 | Ogura | ................ | G06K 9/00013 382/321 |
| 2004/0051791 A1 * | 3/2004 | Hashimoto | ........ | G06K 9/00013 348/226.1 |
| 2004/0257627 A1 * | 12/2004 | McClurg | ............ | G06K 9/00046 358/509 |
| 2005/0265585 A1 | 12/2005 | Rowe | | |
| 2006/0159317 A1 * | 7/2006 | Shyu | ................ | G06K 9/00046 382/127 |
| 2006/0169159 A1 * | 8/2006 | Reinhold | ........... | G06K 9/00046 101/454 |
| 2007/0116331 A1 * | 5/2007 | Rowe | ................ | G06K 9/00046 382/127 |
| 2007/0160269 A1 * | 7/2007 | Kuo | ................... | G06K 9/00046 382/124 |
| 2007/0253607 A1 * | 11/2007 | Higuchi | ............... | G06K 9/0012 382/124 |
| 2008/0017544 A1 | 1/2008 | Amsden | | |
| 2008/0123908 A1 * | 5/2008 | Waldman | ........... | G06K 9/00046 382/124 |
| 2008/0247613 A1 | 10/2008 | Chang | | |
| 2008/0298649 A1 * | 12/2008 | Ennis | ................... | G06K 9/0012 382/125 |
| 2008/0298650 A1 * | 12/2008 | Jang | ................... | G06K 9/00046 382/127 |
| 2010/0080422 A1 * | 4/2010 | Sato | ..................... | G06K 9/0004 382/115 |
| 2010/0110170 A1 * | 5/2010 | Bringer | .............. | G06K 9/00067 348/77 |
| 2011/0013074 A1 | 1/2011 | Ichimura et al. | | |
| 2011/0015709 A1 | 1/2011 | Vogt et al. | | |
| 2011/0150304 A1 * | 6/2011 | Abe | ..................... | A61B 5/1172 382/124 |
| 2012/0070043 A1 * | 3/2012 | Higuchi | ............... | G06K 9/0012 382/124 |
| 2012/0087555 A1 * | 4/2012 | Dumont | .................. | G06K 9/00 382/127 |

FOREIGN PATENT DOCUMENTS

| | | |
|---|---|---|
| CN | 101201896 A | 6/2008 |
| CN | 101226589 A | 7/2008 |
| CN | 101408938 A | 4/2009 |
| CN | 101441711 A | 5/2009 |
| CN | 101506827 A | 8/2009 |
| CN | 101953689 A | 1/2011 |
| CN | 201716741 U | 1/2011 |
| JP | 2006-065400 A | 3/2006 |
| JP | 2007-122237 A | 5/2007 |
| JP | 2007-179434 A | 7/2007 |
| JP | 2007-259964 A | 10/2007 |
| JP | 2008-501196 A | 1/2008 |
| JP | 2008-067727 A | 3/2008 |
| JP | 2010-503079 A | 1/2010 |
| JP | 2010-521206 A | 6/2010 |
| JP | 2010-282519 A | 12/2010 |

OTHER PUBLICATIONS

Japanese Office Action for JP Application No. 2013-507459 dated Jan. 28, 2015 with English Translation.
Chinese Office Action for CN Application No. 201280015009.9 dated Nov. 3, 2015.
Japanese Office Action for JP Application No. 2015-184510 dated Aug. 24, 2016 with English Translation.
Chinese Office Action for JP Application No. 201280015009.9 dated Aug. 21, 2017 with English Translation.
U.S. Office Action for U.S. Appl. No. 15/854,217 dated Nov. 25, 2019.
U.S. Office Action for U.S. Appl. No. 16/124,721 dated Nov. 27, 2019.
U.S. Office Action for U.S. Appl. No. 16/124,914 dated Jan. 9, 2020.
U.S. Office Action and PTO-892 for U.S. Appl. No. 16/124,914 datd Jul. 28, 2020.

* cited by examiner

AUTHENTICATION USING PRISM

CROSS-REFERENCE TO RELATED APPLICATIONS

The present application is continuation application of U.S. patent application Ser. No. 15/854,217 filed on Dec. 26, 2017, which is a continuation application of U.S. patent application Ser. No. 14/007,177 filed on Sep. 24, 2013, which is a National Stage Entry of international application PCT/JP2012/057346, filed Mar. 22, 2012, which claims the benefit of priority from Japanese Patent Application 2011-068705 filed on Mar. 25, 2011, the disclosures of all of which are incorporated in their entirety by reference herein.

TECHNICAL FIELD

The present invention relates to an authentication apparatus and an authentication method.

BACKGROUND ART

The apparatus for determining a subject as a forged finger when the color of the image acquired by reflecting visible light of forgery-determining illumination on the subject does not coincide with that of the finger image that has been acquired likewise and has been previously registered in a data storing means is described in Patent literature 1. The same apparatus collates a characteristic point obtained from the transmitted light by radiating near-infrared ray of individual identification illumination to the finger with the characteristic point of the finger image that has been acquired likewise and has been previously registered into the data storing means, and performs the individual identification.

The apparatus for selectively switching white light and infrared light, reflecting the white light on a surface layer portion of the finger thereby to acquire the fingerprint image, making the infrared ray incident inside the finger and scattering the infrared ray thereby to acquire a vein image, comparing the fingerprint image and the vein image with the registered fingerprint image and the registered vein image, respectively, and authenticating a specific personal is described in Patent literature 2.

The apparatus for comparing the fingerprint image with high sensitivity with the fingerprint image with low sensitivity, and determining the forged finger is described in Patent literature 3.

The apparatus for, based on a difference of the finger vein images imaged with the transmitted lights having a different wavelength, determining whether the above finger vein image is the finger vein image of a living body is described in Patent literature 4.

On the other hand, the technique of using a prism as a scanner for the fingerprint authentication, and augmenting a contrast is described in Patent literature 5.

CITATION LIST

Patent Literature

PTL 1: JP-P2007-122237A
PTL 2: JP-P2007-179434A
PTL 3: JP-P2007-259964A
PTL 4: JP-P2008-67727A
PTL 5: U.S. Pat. No. 6,381,347

SUMMARY OF INVENTION

Technical Problem

By the way, in recent years, it is difficult to see through the action such as "impersonating" others by affixing a semi-transparent forged film of the finger having concave and convex to the tip of the genuine finger. Such a malicious action is also done by use of the finger forged with resin such as silicon having concave and convex.

However, any of the above-described Patent literatures 1 to 4 cannot detect the forgery of the above finger at a high precision using the reflected light image and the transmitted light image that are obtained from the identical finger.

Further, the technology of the Patent literature 5 as well can obtain the image with a high contrast necessary for the collation of the fingerprint; however, the Patent literature 5 cannot detect the forgery of the finger at a high precision similarly to the technologies of the above-described Patent literatures 1 to 4 because only the image of the portion having contacted the prism is obtained.

Thereupon, the present invention has been accomplished in consideration of the above-mentioned problems, and an object of the present invention is to provide an authentication apparatus and an authentication method capable of acquiring the fingerprint image having a contrast enough for collating the fingerprint and a natural image of the finger that is close to visibility.

Solution to Problem

The present invention is an authentication apparatus comprising: a prism of an approximately quadrangle-frustum shape, said prism of the approximately quadrangle-frustum shape is arranged so that a bottom side, out of two parallel surfaces of said prism of approximately quadrangle-frustum shape, is a placing surface side for a finger; a first imaging means is arranged below a top surface parallel to said bottom surface, said first imaging means that images an image of the finger transmitted through said top surface; a light source that radiates light to at least one side surface of a first set of side surfaces, out of two sets of side surfaces of said approximately quadrangle-frustum shape that face each other; and a second imaging means that images the image of the finger transmitted through a second set of side surfaces, out of said two sets of side surfaces.

The present invention is an authentication method comprising: arranging a prism of an approximately quadrangle-frustum shape so that a bottom side, out of two parallel surfaces of the approximately quadrangle-frustum shape, is a placing surface side for a finger; radiating light from at least one side surface of a first set of side surfaces, out of two sets of side surfaces of said approximately quadrangle-frustum shape that face each other; and from a lower part of a top surface parallel to said bottom surface, imaging an image of the finger transmitted through said top surface; imaging the image of the finger transmitted through a second set of side surfaces, out of said two sets of side surfaces; and simultaneously imaging a natural image of the finger and the image of a fingerprint portion.

Advantageous Effect of Invention

The present invention makes it possible to acquire the fingerprint image having a contrast enough for collating the fingerprint and the natural image that is close to visibility.

DESCRIPTION OF EMBODIMENTS

The exemplary embodiments of the present invention will be explained.

Figure 1:
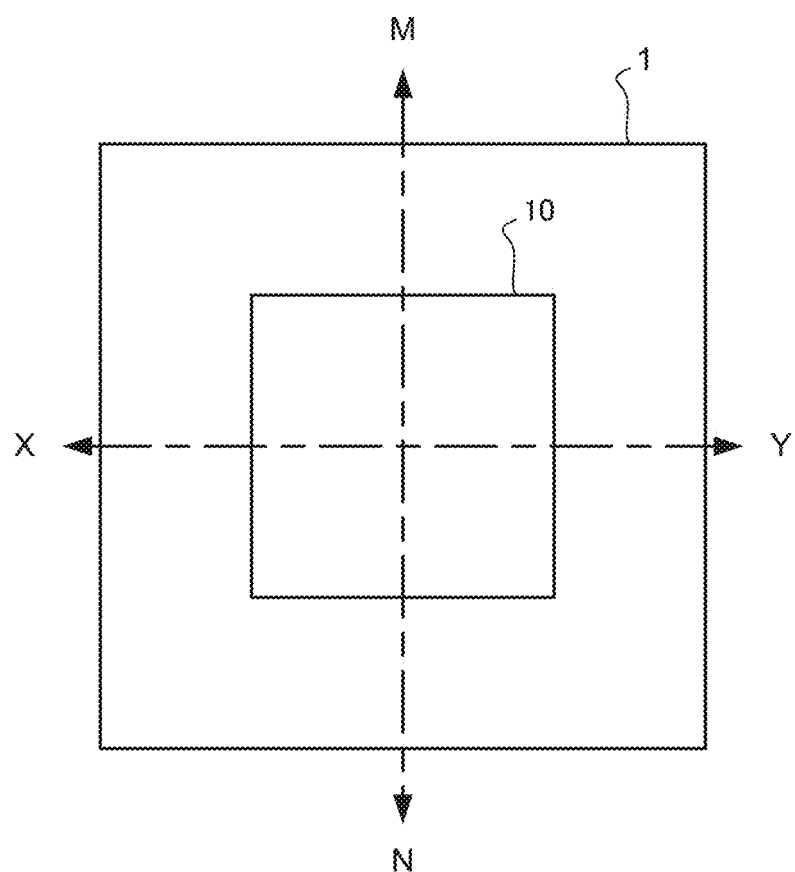
FIG. 1 is a top view of a living body authentication apparatus in a first exemplary embodiment.
Figure 2:
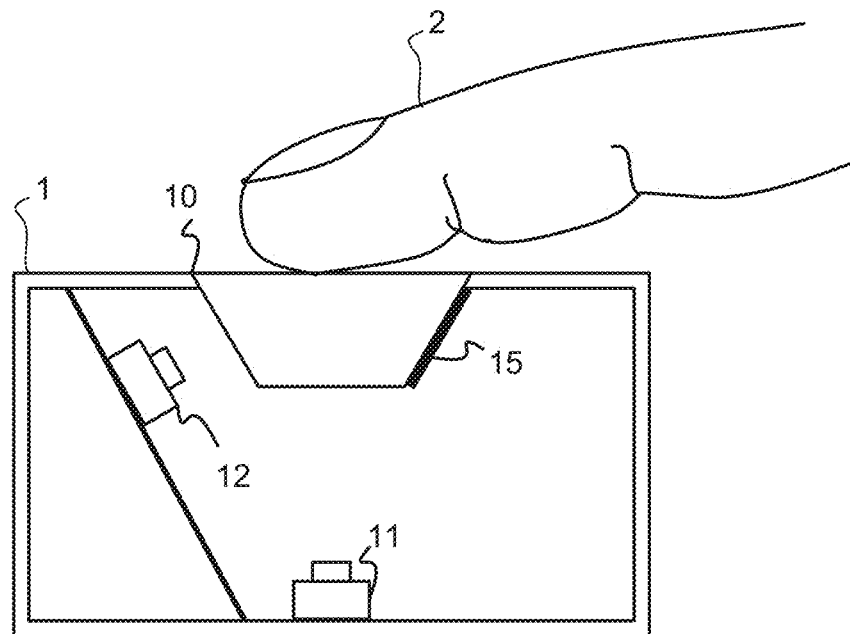
FIG. 2 is a cross-sectional view of M-N of the living body authentication apparatus.
Figure 3:
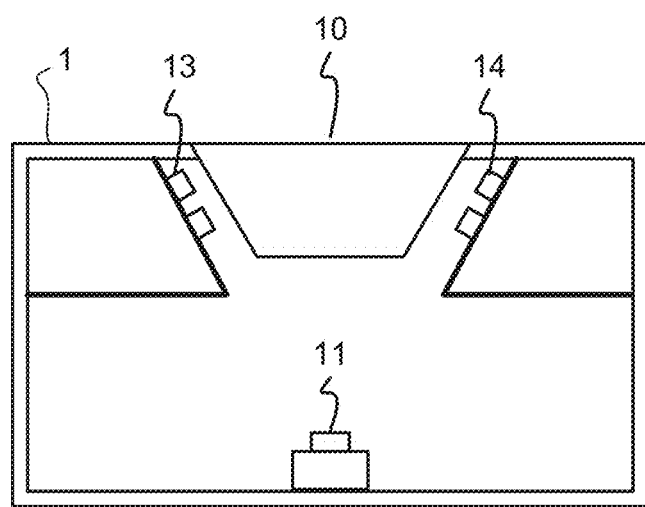
FIG. 3 is a cross-sectional view of X-Y of the living body authentication apparatus.

Each of FIG. 1, FIG. 2, and FIG. 3 is a view for explaining the living body authentication apparatus in the first exemplary embodiment, FIG. 1 is a top view of the living body authentication apparatus in the first exemplary embodiment, FIG. 2 is a cross-sectional view of M-N of the living body authentication apparatus, and FIG. 3 is a cross-sectional view of X-Y of the living body authentication apparatus.

The regular quadrangle-frustum shape type prism 10 is arranged into a living body authentication apparatus 1 of the first exemplary embodiment.

Figure 4:
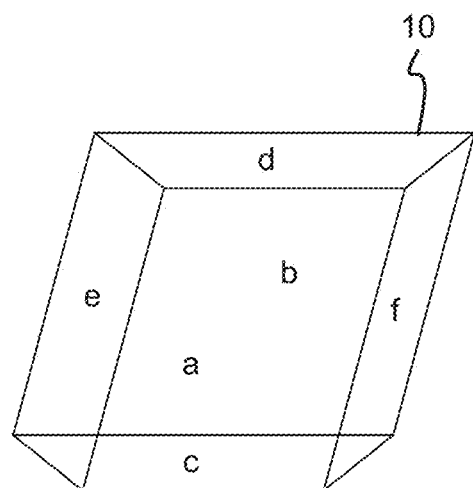
FIG. 4 is a view for explaining a regular quadrangle-frustum shape type prism 10 to be used for the living body authentication apparatus of the first exemplary embodiment.

FIG. 4 is a view for explaining the regular quadrangle-frustum shape type prism 10 to be used for the living body authentication apparatus of the first exemplary embodiment. The regular quadrangle-frustum shape type prism 10 is arranged so that one surface a (bottom surface (surface having a larger area)), out of two parallel plate-shape surfaces a and b, is a placing surface of the fingerprint. Additionally, an example of defining the type of the prism 10 as the regular quadrangle-frustum shape type prism is explained in the first exemplary embodiment; however, the shape may be changed without departing from the spirit and scope of the invention.

Further, a first imaging unit 11 that images the image of a finger 2 transmitted through the surface b (top surface (surface having a smaller area) of the prism 10 is arranged in the lower part of the surface b of the prism 10. As the imaging unit 11, which converts the inputted image into a digital signal and outputs it, an image sensor comprised of CCD, or CMOS etc. can be also used. This imaging unit 11 images the natural image of the finger by the light transmitted through the surface b of the prism 10, and obtains the image for determining the forged finger.

Light sources 13 and 14 that radiate the light to the fingerprint portion of the finger 2 are installed in the side surfaces c and d sides of the prism 10 that face each other, respectively. These light sources 13 and 14 are white LEDs emitting visible light, for example, the white light, and the like.

Further, in one side surface e side, out of side surfaces e and f of the prism 10 that face each other, a second imaging unit 12 that images the finger portion of the finger 2 transmitted through the side surface e is arranged. As the imaging unit 12, which converts the inputted image into a digital signal and outputs it, an image sensor comprised of CCD, or CMOS etc. can be also used. This imaging unit 12 images the fingerprint collation image of the fingerprint portion of the finger 2 having a high contrast (a mountain and a valley of the fingerprint are clear) by the light transmitted through the side surface e.

On the other side, a black shielding plate 15 that does not allow the light to be transmitted is installed in the surface f. This shielding plate 15 allows the fingerprint collation image imaged by the imaging unit 12 to become an image with a higher contrast. Additionally, in this exemplary embodiment, the black shielding plate 15 was installed in the surface f; however, the outer surface of the surface f of the prism 10 may be pained in a block color.

Next, an operation of the above-mentioned living body authentication apparatus will be explained.

At first, the finger 2 is placed on the surface a of the prism 10, being a placing surface, at the moment of the authentication.

The light sources 13 and 14 emits the light in a situation in which the fingerprint portion of the finger 2 is placed on the surface a of the prism 10, and radiates the light for photography to the surfaces c and d of the prism 10, respectively.

Figure 5:
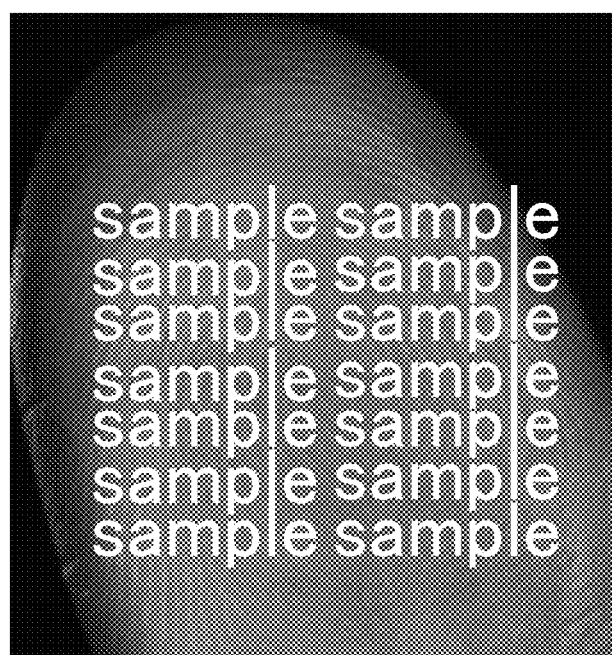
FIG. 5 is a view for explaining the first exemplary embodiment.

The imaging unit 11 images the natural image of the finger by the light transmitted through the surface b of the prism 10. One example of the image imaged by the imaging unit 11 is shown in FIG. 5. As apparent from FIG. 5, it can be grasped that the natural image of the finger 2 including the fingerprint portion is imaged. Displaying the image imaged by this imaging unit 11 on a display device, and visually confirming it makes it possible to determine whether a fingerprint film, a tape and the like forged at the moment of the collation have been used.

Figure 6:
FIG. 6 is a view for explaining the first exemplary embodiment.

On the other hand, the imaging unit 12 images the image of the fingerprint portion of the finger 2 by the light transmitted through the surface e. One example of the image imaged by the imaging unit 12 is shown in FIG. 6. As apparent from FIG. 6, it can be grasped that the image of the fingerprint portion having a high contrast (a mountain and a valley of the fingerprint are clear) has been photographed. Performing the extraction/collation of a characteristic quantity from the image imaged by this imaging unit 12 makes it possible to collate and authenticate the fingerprint.

In such a manner, the authentication apparatus of the first exemplary embodiment can obtain the natural image close to the visibility for determining whether the forged fingerprint film and tape, and the like have been used, and the image having a high contrast to be used for collating the fingerprint with one-time photography of the finger.

Second Exemplary Embodiment

The second exemplary embodiment will be explained.

Figure 7:
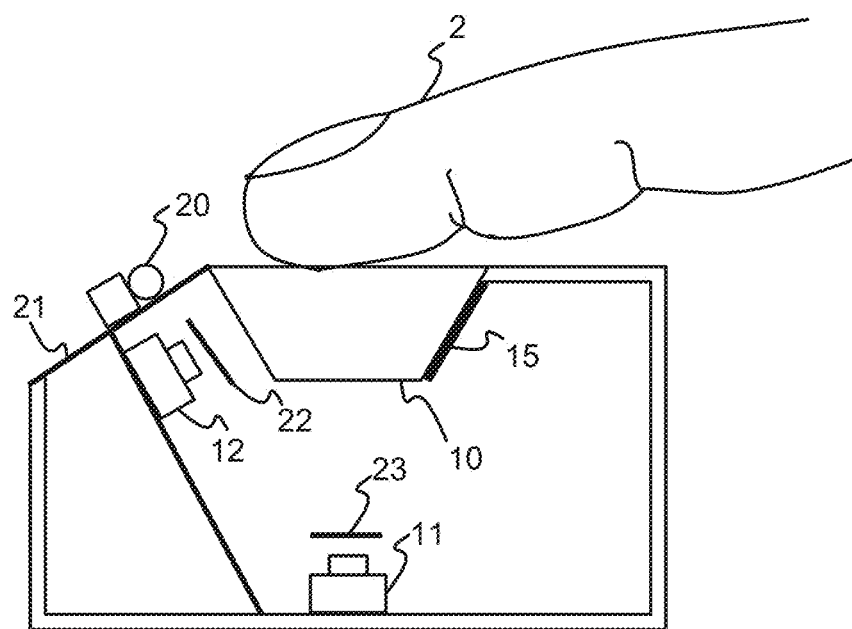
FIG. 7 is a cross-sectional configuration view of the authentication apparatus in a second exemplary embodiment.

FIG. 7 is a cross-sectional configuration view of the authentication apparatus in the second exemplary embodiment.

In the second exemplary embodiment, an example of installing an infrared ray light source 20 in addition to the configuration of the first exemplary embodiment, and imaging the fingerprint image by the light that scatters inside the finger, and is transmitted will be explained.

In the second exemplary embodiment, the infrared ray light source 20 is arranged in the authentication apparatus. The infrared ray light source 20 is arranged on a shielding plate 21 so that the infrared-ray light does not enter the prism 10 if possible. Further, an infrared ray transmission filter 22 is i arranged in the imaging unit 12. Making such a configuration enables the imaging unit 12 to image the image of the fingerprint portion with a high contrast (a mountain and a valley of the fingerprint are clear) as compared with the image imaged only by light sources 13 and 14 such as the while light etc.

Figure 8:
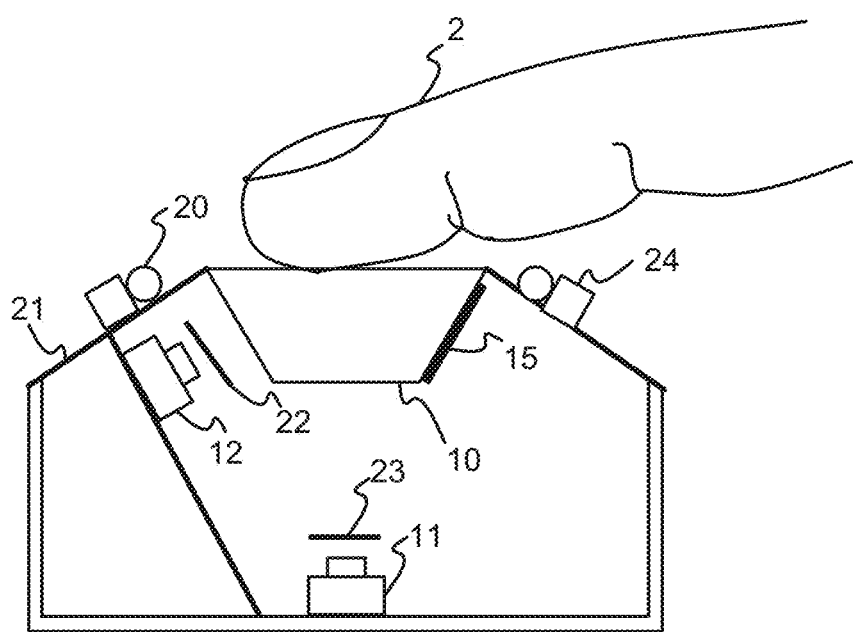
FIG. 8 is a cross-sectional configuration view of the authentication apparatus in the second exemplary embodiment.

In addition, as shown in FIG. 8, an infrared ray light source 24 for irradiating a root portion of the finger 2 may be arranged in addition to the infrared ray light source 20. Installing the infrared ray light source 24 for irradiating the root portion of the finger 2 makes it possible to obtain the image of the fingerprint portion that is bright also in a root side of the fingerprint. Additionally, the infrared light is absorbed with hemoglobin of blood, whereby a blood vessel pattern of the finger 2 can be also imaged.

In order to photograph the natural image for determining whether the forged fingerprint film and tape, and the like have been used, an infrared ray cut-off filter 23 is arranged in the imaging unit 11. With regard to the lights incident on the imaging unit 11, the infrared ray is cut off by the infrared ray cut-off filter 23, and the imaging unit 11 can image the natural image of the fingerprint portion of the finger 2 by the visible light owing to the light sources 13 and 14.

In accordance with the second exemplary embodiment, the fingerprint image having a high contrast by the light that scatters inside the finger due to the infrared light source and is transmitted in addition to the effect of the first exemplary embodiment can be obtained. Further, a pulse beat caused by a blood flow and a change in the image due to a subcutaneous tissue are also can be observed, and the living body determination with a higher precision can be also performed by using it for the living body determination.

Further, the content of the above-mentioned exemplary embodiments can be expressed as follows.

(Supplementary note 1) An authentication apparatus comprising:

a prism of an approximately quadrangle-frustum shape, said prism of the approximately quadrangle-frustum shape is arranged so that a bottom side, out of two parallel surfaces of said prism of approximately quadrangle-frustum shape, is a placing surface side for a finger;

a first imaging means is arranged below a top surface parallel to said bottom surface, said first imaging means that images an image of the finger transmitted through said top surface;

a light source that radiates light to at least one side surface of a first set of side surfaces, out of two sets of side surfaces of said approximately quadrangle-frustum shape that face each other; and a second imaging means that images the image of the finger transmitted through a second set of side surfaces, out of said two sets of side surfaces.

(Supplementary note 2) The authentication apparatus according to Supplementary note 1, wherein said prism is a regular quadrangle-frustum.

(Supplementary note 3) The authentication apparatus according to Supplementary note 1 or Supplementary note 2, wherein a black plate is installed in the side surface facing the side surface to be arranged in said second imaging means, out of said second sets of side surfaces of said prism, or an color of an outer surface of said side surface is black.

(Supplementary note 4) The authentication apparatus according to one of Supplementary note 1 to Supplementary note 3, comprising:

an infrared light source that radiates infrared ray light to a cushion portion of the finger;

an infrared ray cut-off filter that cuts off the infrared ray light incident on said first imaging means; and a visible light cut-off filter that cuts off visible light incident on said second imaging means.

(Supplementary note 5) An authentication method comprising:

arranging a prism of an approximately quadrangle-frustum shape so that a bottom side, out of two parallel surfaces of the approximately quadrangle-frustum shape, is a placing surface side for a finger;

radiating light from at least one side surface of a first set of side surfaces, out of two sets of side surfaces of said approximately quadrangle-frustum shape that face each other; and from a lower part of a top surface parallel to said bottom surface, imaging an image of the finger transmitted through said top surface;

imaging the image of the finger transmitted through a second set of side surfaces, out of said two sets of side surfaces; and simultaneously imaging a natural image of the finger and the image of a fingerprint portion.

(Supplementary note 6) The authentication method according to Supplementary note 5, wherein said prism is regular quadrangle-frustum.

(Supplementary note 7) The authentication method according to Supplementary note 5 or Supplementary note 6, comprising enhancing a contrast of the image of the fingerprint portion by installing a black plate in the surface of the side facing the surface side in which the image is imaged, out of said second sets of side surfaces of said prism, or making an color of an outer surface of said side surface black.

(Supplementary note 8) The authentication method according to one of Supplementary note 5 to Supplementary note 7, comprising:

radiating visible light from at least one side surface of the first set of side surfaces, out of two sets of side surfaces of said approximately quadrangle-frustum shape that face each other, radiating infrared ray light to a cushion portion of the finger;

cutting off the infrared ray light, out of transmitted lights that are transmitted through an top surface parallel to said bottom surface, and imaging the natural image of the finger by the visible light; and cutting off the visible light, out of transmitted lights that are transmitted through the second set of side surfaces, out of said two sets of side surfaces, and imaging the image of the fingerprint portion of the finger by the infrared ray light.

Above, although the present invention has been particularly described with reference to the preferred embodiments, it should be readily apparent to those of ordinary skill in the art that the present invention is not always limited to the above-mentioned embodiments, and changes and modifications in the form and details may be made without departing from the spirit and scope of the invention.

This application is based upon and claims the benefit of priority from Japanese patent application No. 2011-068705, filed on Mar. 25, 2011, the disclosure of which is incorporated herein in its entirety by reference.

REFERENCE SIGNS LIST 1 living body authentication apparatus
10 prism
11 and 12 imaging units
13 and 14 light sources
15 shielding plate
20 and 24 infrared ray light sources
21 shielding plate
22 infrared ray transmission filter
23 infrared ray cut-off filter

The invention claimed is:

1. An apparatus comprising:
a prism including a large surface at least a portion of which is a placing region for a finger, a small surface parallel to the large surface, a first inclined lateral surface and a second inclined lateral surface;
a light source that emits light to the first inclined lateral surface;
a first infrared light source arranged such that a first infrared ray light is incident on a portion of the finger not having contacted with the placing region for the finger, the first infrared light source emitting the first infrared ray light;
a second infrared light source arranged on a side opposite to the first infrared light source with respect to the prism and such that a second infrared ray light is incident on the portion of the finger not having contacted with the placing region for the finger, the second infrared light source emitting the second infrared ray light;
a first imaging sensor arranged below the small surface, the first imaging sensor receiving a light transmitted from the light source through the small surface to obtain a first image of finger;
a second imaging sensor receiving light transmitted from the light source, the first infrared light source and the second infrared light source through the second inclined lateral surface to obtain a second image of finger of which fingerprint pattern contrast is enhanced more than fingerprint pattern contrast of the first image; and
wherein the second imaging sensor receives the first infrared ray light and the second infrared ray light transmitted from the first infrared light source and the second infrared light source through the second inclined lateral surface to obtain a third image for a blood vessel of the finger.

2. The apparatus according to claim 1, wherein
a black plate is installed in the side surface facing the second inclined lateral surface, or a color of an outer surface of the side surface is black.

3. The apparatus according to claim 1, wherein
the prism is a quadrangle-frustum shape, and
the first inclined lateral surface and the second inclined lateral surface do not face each other.

4. An authentication method using an apparatus, the apparatus comprising:
a prism including a large surface at least a portion of which is a placing region for a finger, a small surface parallel to the large surface, a first inclined lateral surface and a second inclined lateral surface;
a light source;
a first imaging sensor arranged below the small surface;
a second imaging sensor;
a first infrared light source arranged such that a first infrared ray light is incident on a portion of the finger not having contacted with the placing region for the finger, and
a second infrared light source arranged on a side opposite to the first infrared light source with respect to the prism and such that a second infrared ray light is incident on the portion of the finger not having contacted with the placing region for the finger;
the authentication method comprising:
emitting light from the light source to the first inclined lateral surface,
emitting the first infrared ray light from the first infrared light source to the finger,
emitting the second infrared ray light from the second infrared light source to the finger,
receiving, by the first imaging sensor, a light transmitted from the light source through the small surface to obtain a first image of finger,
receiving, by the second imaging sensor, a light transmitted from the light source, the first infrared light source and the second infrared light source through the second inclined lateral surface to obtain a second image of finger of which fingerprint pattern contrast is enhanced more than fingerprint pattern contrast of the first image, and
receiving, by the second imaging sensor, the first infrared ray light and the second infrared ray light transmitted from the first infrared light source and the second infrared light source through the second inclined lateral surface to obtain a third image for a blood vessel of the finger.

5. The authentication method according to claim 4, wherein
a black plate is installed in the side surface facing the second inclined lateral surface, or a color of an outer surface of the side surface is black.

6. The authentication method according to claim 4, wherein
the prism is a quadrangle-frustum shape, and
the first inclined lateral surface and the second inclined lateral surface do not face each other.

7. A non-transitory computer readable medium recording a program that causes a computer to perform an authentication method, the authentication method performed by using an apparatus,
the apparatus comprising:
a prism including a large surface at least a portion of which is a placing region for a finger, a small surface parallel to the large surface, a first inclined lateral surface and a second inclined lateral surface;
a light source;
a first imaging sensor arranged below the small surface;
a second imaging sensor;
a first infrared light source arranged such that a first infrared ray light is incident on a portion of the finger not having contacted with the placing region for the finger; and
a second infrared light source arranged on a side opposite to the first infrared light source with respect to the prism and such that a second infrared ray light is incident on the portion of the finger not having contacted with the placing region for the finger, the program causing the computer to perform:
emitting light from the light source to the first inclined lateral surface,
emitting the first infrared ray light from the first infrared light source to the finger,
emitting the second infrared ray light from the second infrared light source to the finger,
receiving, by the first imaging sensor, a light transmitted from the light source through the small surface to obtain a first image of finger,
receiving, by the second imaging sensor, a light transmitted from the light source, the first infrared light source and the second infrared light source through the second inclined lateral surface to obtain a second image of finger of which fingerprint pattern contrast is enhanced more than fingerprint pattern contrast of the first image, and
receiving, by the second imaging sensor, the first infrared ray light and the second infrared ray light transmitted from the first infrared light source and the second infrared light source through the second inclined lateral surface to obtain a third image for a blood vessel of the finger.

8. The non-transitory computer readable medium according to claim 7, wherein
a black plate is installed in the side surface facing the second inclined lateral surface, or a color of an outer surface of the side surface is black.

9. The non-transitory computer readable medium according to claim 7, wherein
the prism is a quadrangle-frustum shape, and
the first inclined lateral surface and the second inclined lateral surface do not face each other.

10. The apparatus according to claim 1, wherein
an infrared ray cut-off filter is arranged between the first image sensor and the prism,
an infrared ray transmission filter is arranged between the second image sensor and the prism.

11. The authentication method according to claim 4, wherein
an infrared ray cut-off filter is arranged between the first image sensor and the prism,
an infrared ray transmission filter is arranged between the second image sensor and the prism.

12. The non-transitory computer readable medium according to claim 7, wherein
an infrared ray cut-off filter is arranged between the first image sensor and the prism,
an infrared ray transmission filter is arranged between the second image sensor and the prism.

* * * * *